US012797577B2

(12) United States Patent
Toyoda et al.

(10) Patent No.: US 12,797,577 B2
(45) Date of Patent: Nov. 17, 2026

(54) DELIVERY DEVICE

(71) Applicant: Japan Lifeline Co., Ltd., Tokyo (JP)

(72) Inventors: Yuki Toyoda, Tokyo (JP); Eiichi Nakano, Tokyo (JP)

(73) Assignee: Japan Lifeline Co., Ltd., Tokyo (JP)

( * ) Notice: Subject to any disclaimer, the term of this patent is extended or adjusted under 35 U.S.C. 154(b) by 379 days.

(21) Appl. No.: 18/592,064

(22) Filed: Feb. 29, 2024

(65) Prior Publication Data

US 2024/0316311 A1 Sep. 26, 2024

(30) Foreign Application Priority Data

Mar. 22, 2023 (JP) ................................ 2023-045311

(51) Int. Cl.
*A61M 25/00* (2006.01)
*A61M 25/01* (2006.01)

(52) U.S. Cl.
CPC .... *A61M 25/0017* (2013.01); *A61M 25/0102* (2013.01)

(58) Field of Classification Search
CPC ...................... A61M 25/0017; A61M 25/0102
See application file for complete search history.

(56) References Cited

U.S. PATENT DOCUMENTS

2017/0165065 A1* 6/2017 Rothstein .............. A61F 2/2469

FOREIGN PATENT DOCUMENTS

JP 2018501043 A 1/2018

OTHER PUBLICATIONS

Office Action issued for corresponding Japanese Patent Application No. 2023-045311 dated May 7, 2025; pp. 1-4.

* cited by examiner

*Primary Examiner* — Dung T Ulsh
(74) *Attorney, Agent, or Firm* — Shih IP Law Group, PLLC

(57) ABSTRACT

A delivery device includes: an indwelling device including a stent body that is self-expandable; and a delivery catheter configured to separably support the indwelling device. The delivery catheter includes: a cover configured to cover at least a part of an axial range of the stent body; and an expansion restraining mechanism including a plurality of restraining wire rods configured to restrain expansion of the stent body by hooking a stent wire rod that constitutes the stent body. The plurality of restraining wire rods are configured to release restraint of the stent body by moving axially.

8 Claims, 18 Drawing Sheets

DELIVERY DEVICE

CROSS-REFERENCE TO RELATED APPLICATIONS

This application claims the benefit of priority to Japanese Patent Application Number 2023-045311 filed on Mar. 22, 2023. The entire contents of the above-identified application are hereby incorporated by reference.

TECHNICAL FIELD

The present disclosure relates to a delivery device for delivering an indwelling device to a target site in a body.

BACKGROUND

JP 2018-501043 A discloses a delivery device including a self-expandable stent body and a delivery catheter that separably supports the stent body.

SUMMARY

The stent body may be covered with a cover to restrain the expansion of the stent body. When a stent body is covered with a cover, the expanding force of the stent body may cause the axial end of the cover to be displaced on the inner side in the axial direction, so that a part of the stent body may be unintentionally exposed and then expand. A part of the stent body, when expanding unintentionally, will interfere with the delivery of the indwelling device into a body.

Thus, an object of the present disclosure is to provide a delivery device capable of suppressing displacement of a cover covering a stent body.

A delivery device of the present disclosure includes: an indwelling device including a stent body that is self-expandable; and a delivery catheter configured to separably support the indwelling device. The delivery catheter includes: a cover configured to cover at least a part of an axial range of the stent body; and an expansion restraining mechanism including a plurality of restraining wire rods configured to restrain expansion of the stent body by hooking a stent wire rod that constitutes the stent body. The plurality of restraining wire rods are configured to release the restraint of the stent body by moving in an axial direction.

According to the present disclosure, displacement of the cover covering the stent body can be suppressed.

BRIEF DESCRIPTION OF DRAWINGS

FIG. 7A illustrates a state of the stent body before the start of an exposing motion. FIG. 7B illustrates a state of the stent body during the exposing motion. FIG. 7C illustrates a state of the stent body after the completion of the exposing motion.

FIG. 10A illustrates a state of the delivery catheter before the operation. FIG. 10B illustrates a state of the stent wire rod unhooked.

FIG. 11A illustrates a state of the delivery catheter before the operation.

FIG. 11B illustrates a state immediately after an exposing motion of the stent body is started.

FIG. 11C illustrates a state after the exposure motion of the stent body is completed. FIG. 11D illustrates a state of the stent wire rod unhooked.

DESCRIPTION OF EMBODIMENTS

First Embodiment

Figure 1:
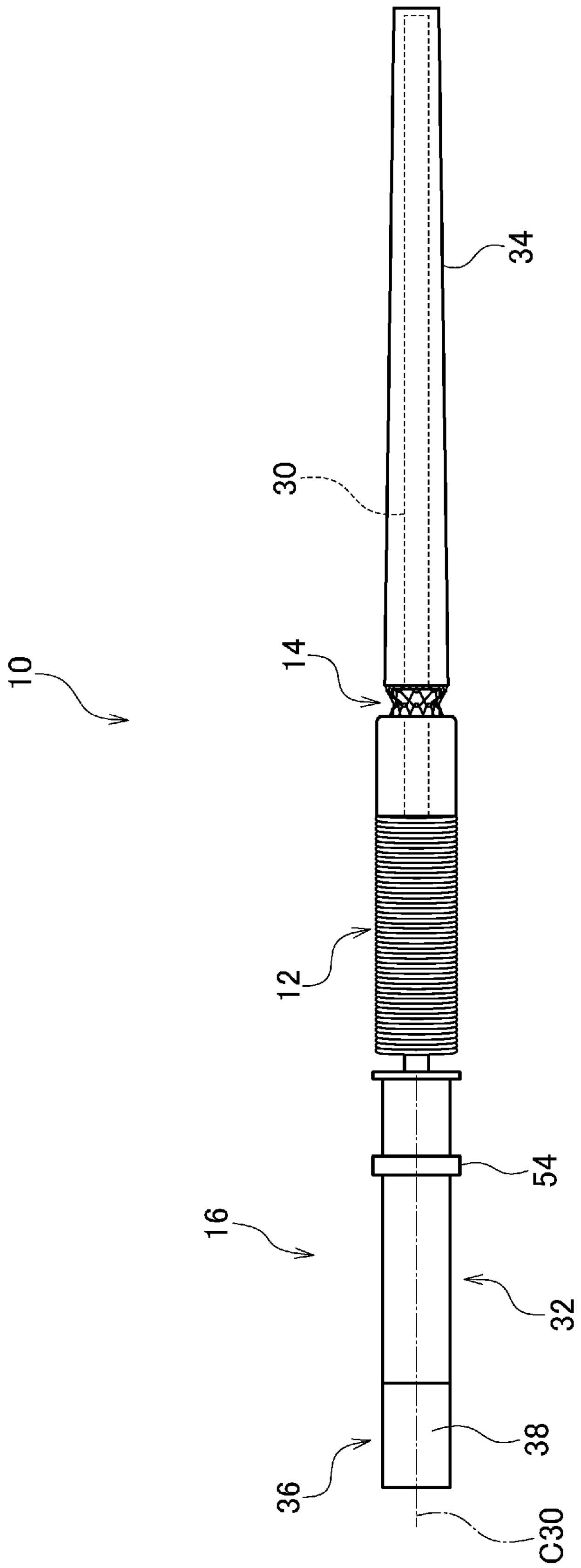
FIG. 1 is a side view of a delivery device of a first embodiment.

Embodiments for implementing a delivery device of the present disclosure are described below. The same or equivalent constituent elements are denoted by the same reference signs, and redundant descriptions are omitted. In the drawings, for convenience of description, components are omitted, enlarged, or reduced, as appropriate. The drawings are to be viewed in accordance with the orientation of the reference signs.

Description will be made with reference to FIG. 1. A delivery device 10 is used to deliver an indwelling device 12 to a target site in the body. The delivery device 10 includes the indwelling device 12 with a stent body 14 that is self-expandable, and a delivery catheter 16 that separably supports the indwelling device 12. In the present specification, a direction along the axis of a shaft 30 of the delivery catheter 16 is simply referred to as an axial direction, and the radial direction and the circumferential direction with that axis as the circle center are simply referred to as a radial direction and a circumferential direction. The side of the shaft 30 away from a handle 32 of the delivery catheter 16 in the axial direction is referred to as a distal end side, and the side opposite in the axial direction is referred to as a proximal end side.

Figure 2:
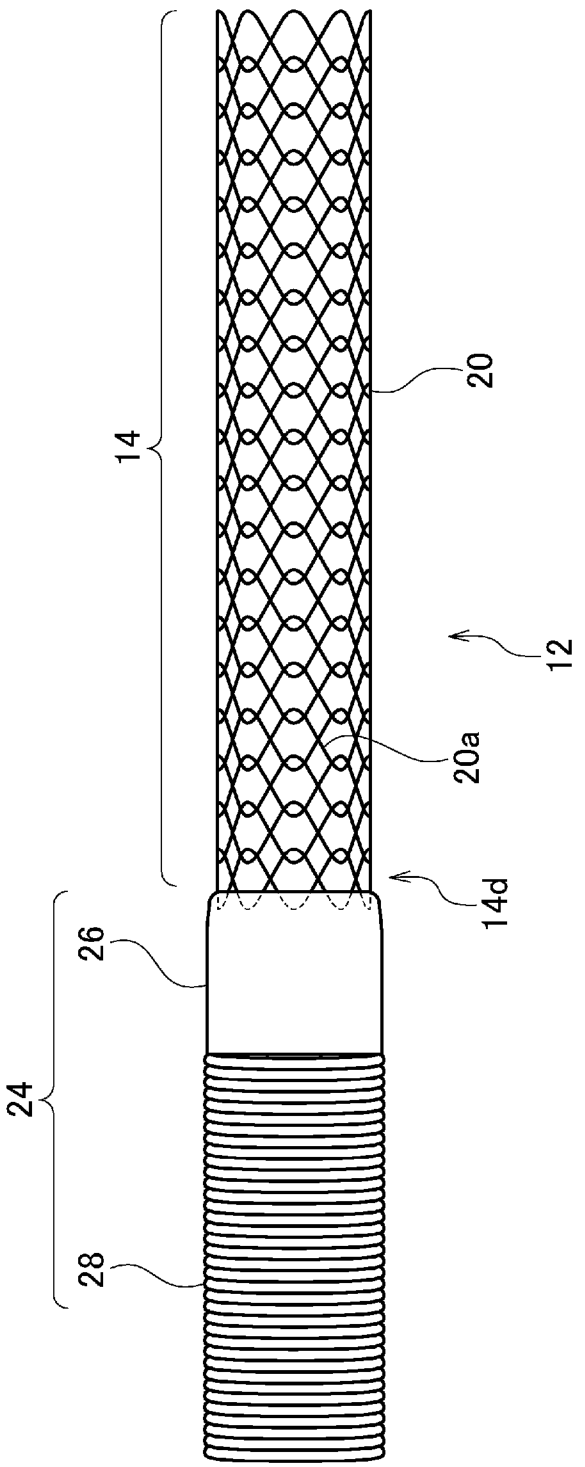
FIG. 2 is a side view of an indwelling device of the first embodiment.
Figure 3:
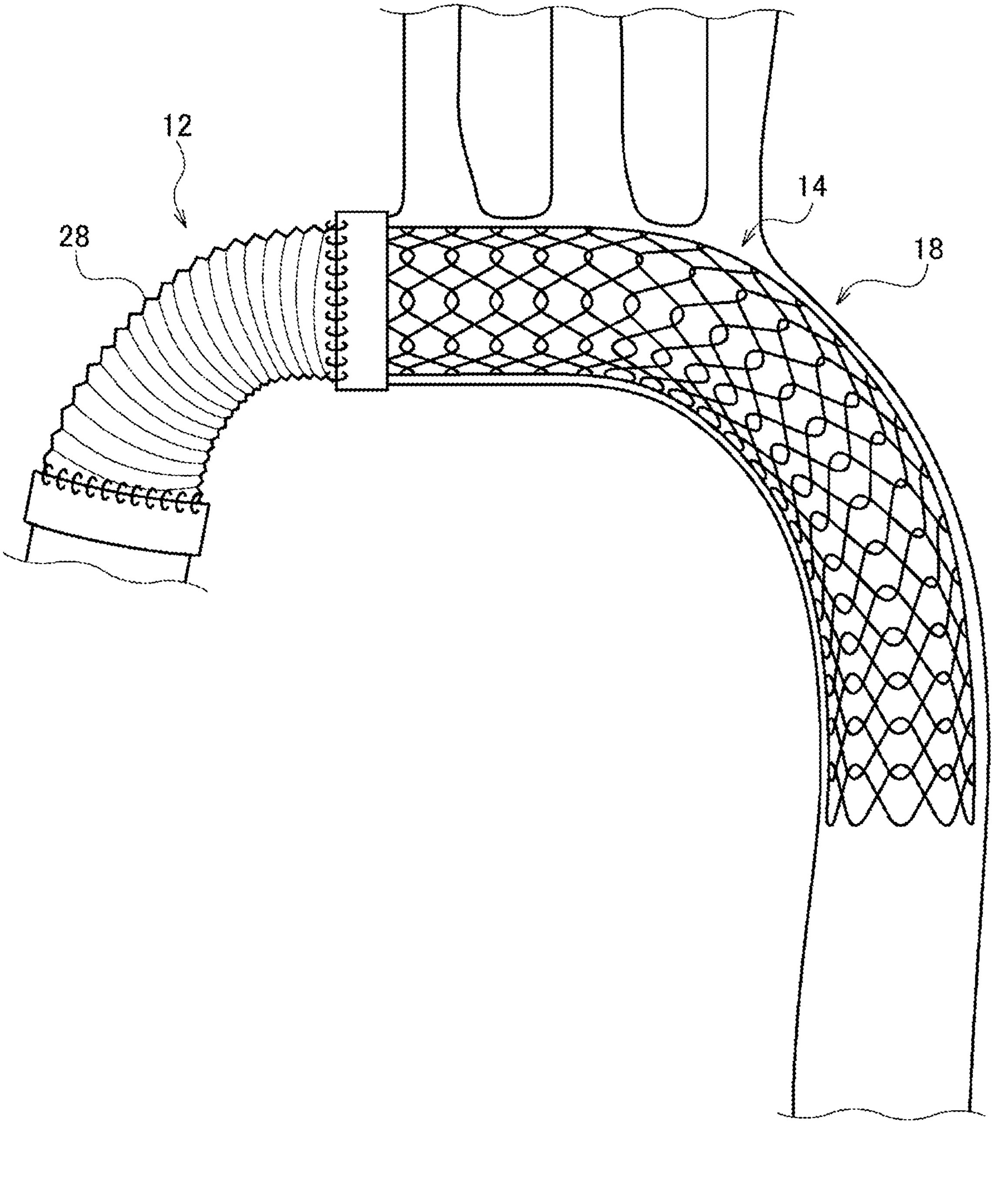
FIG. 3 is a schematic diagram illustrating an example of the use of the indwelling device in the first embodiment.

Description will be made with reference to FIGS. 2 and 3. The indwelling device 12 is placed for treatment at a target site in the body. Here an example will be described in which the indwelling device 12 is used to treat arterial dissection of thoracic aorta 18. In this case, the arterial dissection is treated by pressing the intima of the dissected part against the adventitia with the stent body 14 of the indwelling device 12. The indwelling device 12 is not limited to this application, and may be used for various treatments for an obstruction of an aneurysm and a digestive tract. Specific examples of living organs to be treated are not limited, and applications may include various arteries such as abdominal aorta, iliac artery and femoral artery as well as digestive tract in addition to the thoracic aorta 18.

The operative method using the delivery device 10 of the present embodiment will be described by taking an example of the OSG (Open Stent Grafting) method with undergoing thoracotomy of a living body. The OSG method is a technique in which the indwelling device 12 is inserted through an incision site into a thoracic aorta by using the delivery device 10 after the chest of the living body is opened. The surgical technique using the delivery device 10 is not particularly limited, and may be applied to various techniques such as an EVAR (EndoVascular Aneurysm Repair) technique and a TEVAR (Thoracic EndoVascular Aortic Repair) technique, which do not involve thoracotomy or laparotomy of a living body.

The stent body 14 includes at least one stent 20 that is self-expandable. The term "self-expansion" here refers to expansion on the outer side in the radial direction by the restoring force associated with the elastic deformation of the stent 20. The stent body 14 can remain attached to the luminal surface of the living organ by the self-expanding force of the stent 20. The stents 20 of the present embodiment are composed of braided stents woven in a net-like and tubular shape by using strands 20*a*. As a strand 20*a*, for example, resin in addition to metal such as shape memory alloy and stainless steel, or the like can be used. The stent body 14 of the present embodiment is composed of bare stents using braided stents. Bear stents here are naked stents that are not connected to a graft. The stent body 14 may be made of a stent graft including at least one stent 20 and a graft to which the stent 20 is connected, instead of a bare stent. When the stent body 14 is composed of a stent graft, specific examples of the stent 20 are not limited to braided stents, but may be composed of Z stents, or the like.

The indwelling device 12 includes, as an optional configuration, a tubular body 24 positioned on the proximal end side with respect to the stent body 14 and connected to the stent body 14. The tubular body 24 includes a cuff 26 provided at the distal end portion of the tubular body 24 and a graft 28 provided farther at the proximal end side than the cuff 26. The cuff 26 is positioned inside an opening edge portion provided at an incision site of the thoracic aorta 18 (living organ) and serves as a sewing margin when the graft 28 is anastomosed to the opening edge. The graft 28 is a flexible tubular member that forms a fluid flow channel of such as blood inside. The graft 28 of the present embodiment is used as an artificial blood vessel to replace a part of the resection site (lesion site) of the thoracic aorta 18. A part of a proximal end portion 14*d* of the stent body 14 is inserted inside the tubular body 24 (cuff 26) and connected by sutures, or the like.

Figure 4:
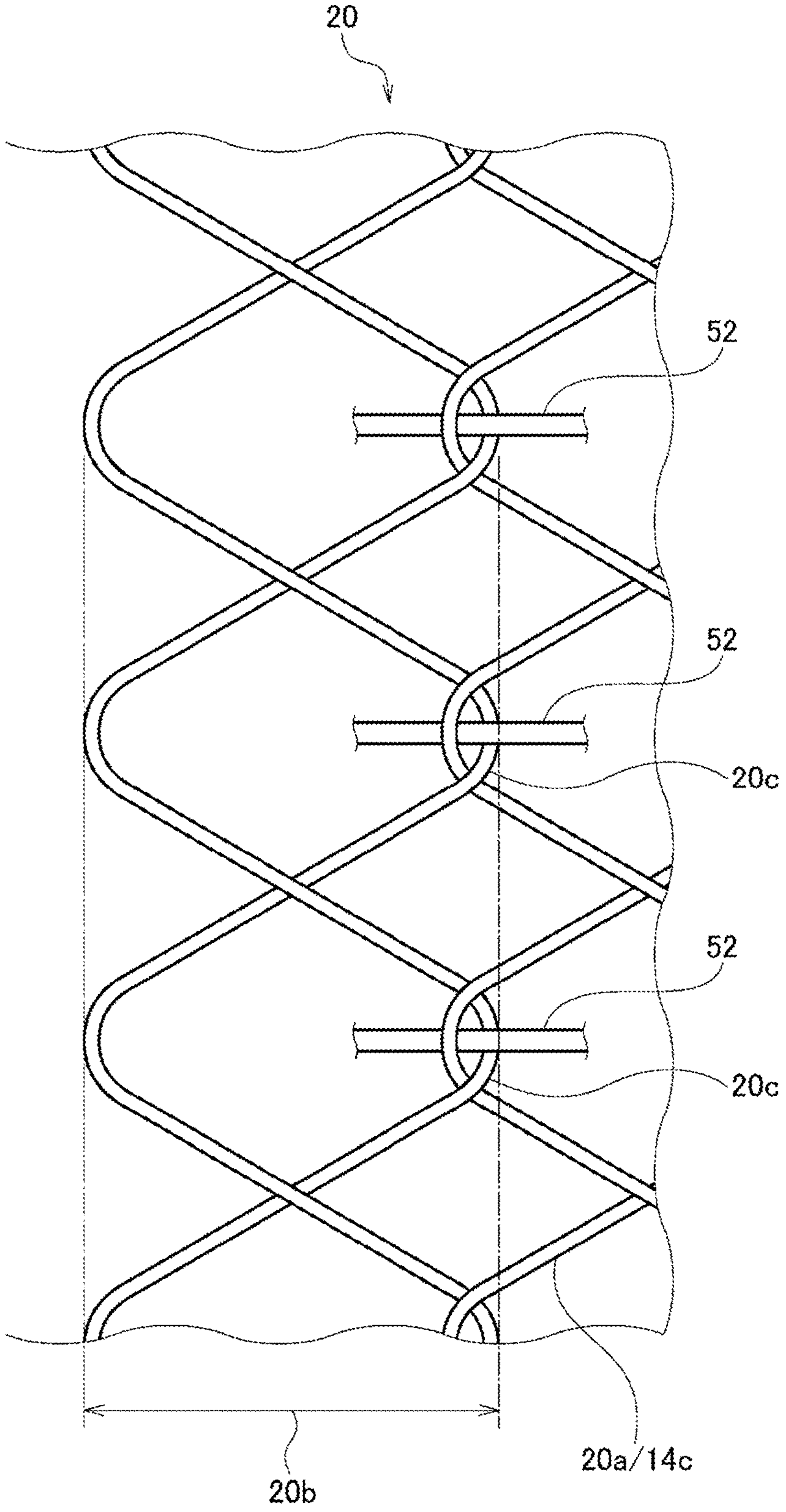
FIG. 4 is a development view illustrating a part of the stent body of the first embodiment.

Description will be made with reference to FIG. 4. FIG. 4 is a development view illustrating a part of the shape of the braided stent constituting the stent body 14, which is cut axially and developed in a plane. The braided stents are composed of unit patterns 20*b*, consisting of the strands 20*a*, arranged in rows in the axial direction. A unit pattern 20*b* is composed of the strand 20*a* which progresses in a wavy pattern in the circumferential direction. The unit pattern 20*b* of the present embodiment is composed of the strand 20*a* that goes around twice in the circumferential direction, and the phase of the wave made by the strand 20*a* on each circumferential direction is shifted by half a pitch toward the circumferential direction. The strand 20*a* constituting the braided stent is provided with a bent part 20*c* that folds toward the circumferential direction in the axial direction. The bent parts 20*c*, formed by the strands 20*a* constituting adjacent patterns 20*b*, is connected by hooking each other. The braided pattern using the strand 20*a* here is an example, and the specific example is not particularly limited. Although a braided pattern using a single strand 20*a* is illustrated here, a braided pattern using a plurality of strands 20*a* may be used.

Figure 5:
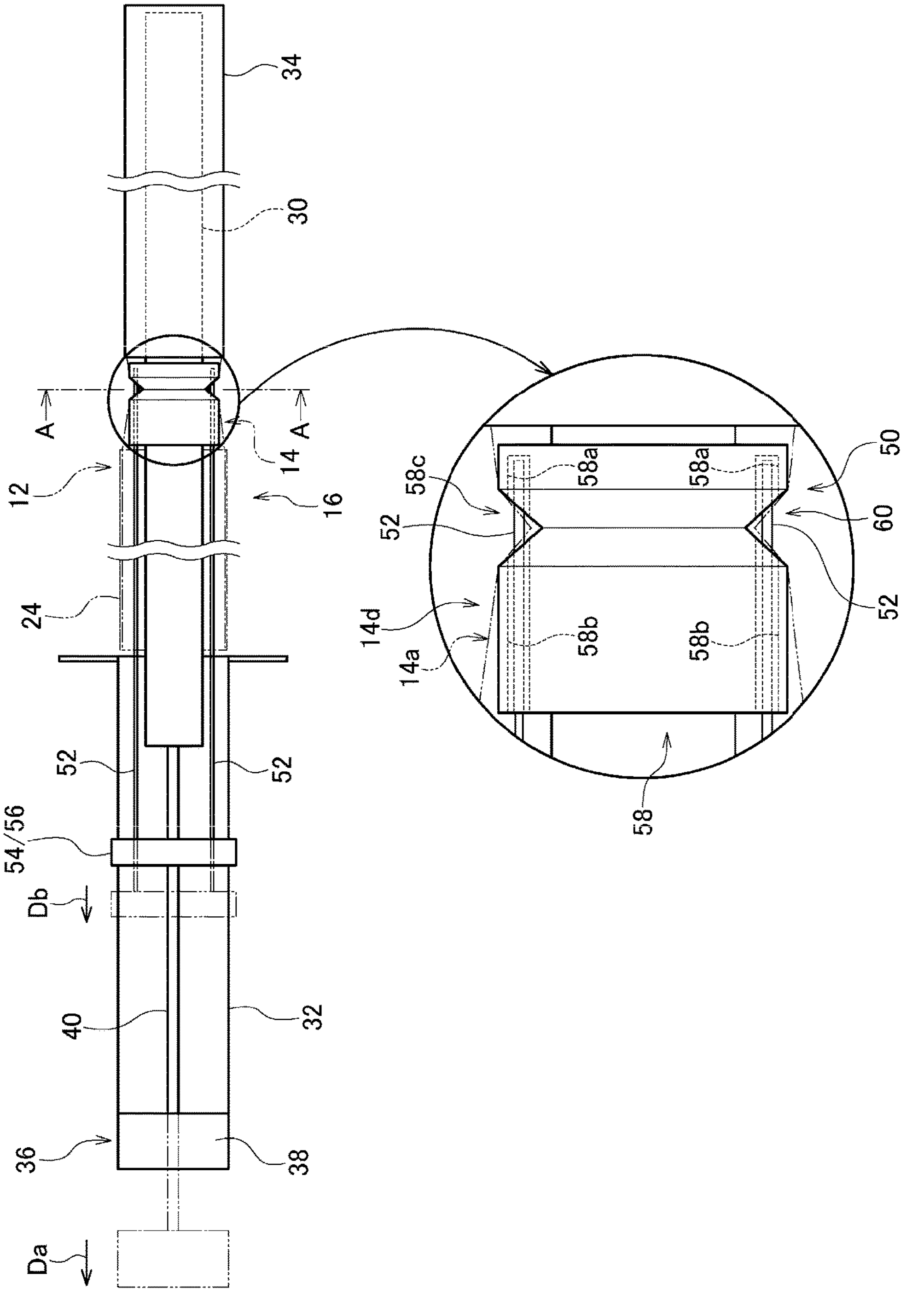
FIG. 5 is a side view schematically illustrating a delivery catheter of the first embodiment.

Description will be made with reference to FIGS. 1 and 5. The delivery catheter 16 includes the shaft 30 that is inserted into the body at least at the distal end side portion, the handle 32 that is attached to the proximal end portion of the shaft 30 and gripped by the operator, a cover 34 that is covered in the axial range of a part of the stent body 14, and a drawing mechanism 36 that pulls the cover 34 axially.

Figure 6:
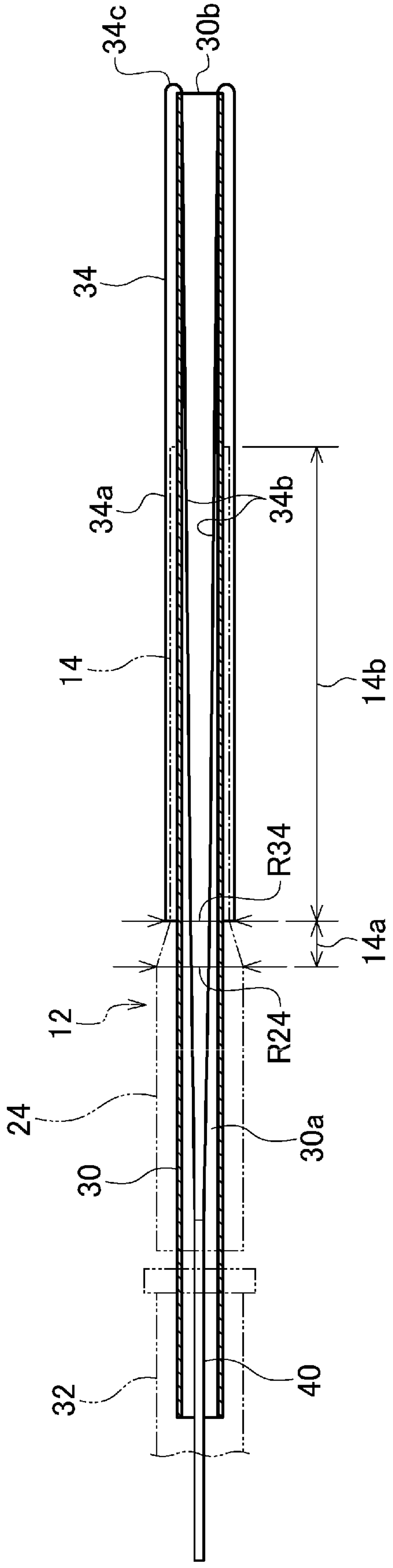
FIG. 6 is a side cross-sectional view illustrating a shaft and a cover of the first embodiment.

Description will be made with reference to FIGS. 5 and 6. The shaft 30 is bendable and deformable. At least a part of the shaft 30 is inserted into the stent body 14 of the indwelling device 12. An axially penetrating hollow part 30*a* is formed inside the shaft 30, and a distal end opening 30*b*, which becomes a part of the hollow part 30*a*, is open at the distal end portion of the shaft 30.

The cover 34 is a tubular body composed of soft material. The cover 34 covers at least a part of the axial range of the stent body 14, and the axial range is maintained in a contracted state. The cover 34 of the present embodiment covers only a part of the axial range of the stent body 14, but may cover the entire axial range of the stent body 14. The cover 34 of the present embodiment has a double structure in which a part of a tubular member is folded inward when the cover 34 is caused to cover the stent body 14. This cover 34 is provided with a tubular outer peripheral part 34*a* covering the stent body 14 from the outer side in the radial direction, an inner part 34*b* inserted inside the stent body 14, and a folded part 34*c* connecting the outer peripheral part 34*a* and the inner part 34*b*. The folded part 34*c* is folded back axially farther at the distal end side than the shaft 30. The outer diameter of the outer peripheral part 34*a* of the cover 34 of the present embodiment gradually decreases toward the distal end side (see FIG. 1). An outer diameter R24 of the distal end portion of the tubular body 24 used for the indwelling device 12 is larger than a maximum outer diameter R34 of the outer peripheral part 34*a* of the cover 34. Here, the maximum outer diameter R34 refers to the outer diameter that becomes the largest in the entire axial range of the outer peripheral part 34*a* of the cover 34.

The drawing mechanism 36 performs an exposing motion by pulling the cover 34 axially to expose the covered part of the stent body 14 by the cover 34. The drawing mechanism 36 is provided with a first operating member 38 receiving an exposing operation Da by the operator for the exposing motion of the stent body 14, and a first traction member 40 pulling the cover 34 to the proximal end side in conjunction with the exposing operation Da with respect to the first operating member 38. The first operating member 38 is operably attached to the handle 32. The first operating member 38 is described here by using a grip as an example, but may be composed of a slide knob, a button, or the like. Furthermore, the exposing operation Da is described with an example made by the axial movement operation of the first operating member 38 toward the proximal end side, but the specific example is not particularly limited and may be a push operation, a rotation operation, or the like. The first traction member 40 is composed of a bar material, wire, or the like. The first traction member 40 includes a distal end portion connected to a part of the cover 34, and a proximal end portion connected to the first operating member 38.

Figure 7A:
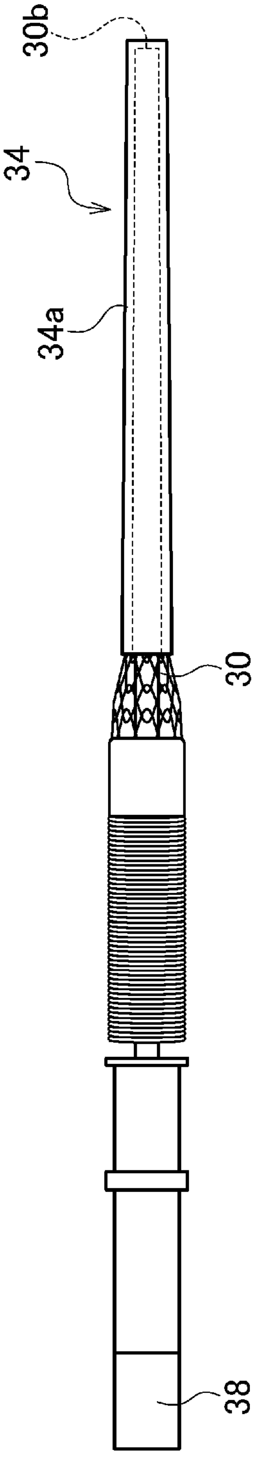
FIGS. 7A to 7C are schematic diagrams illustrating operations of a drawing mechanism of the first embodiment.
Figure 7B:
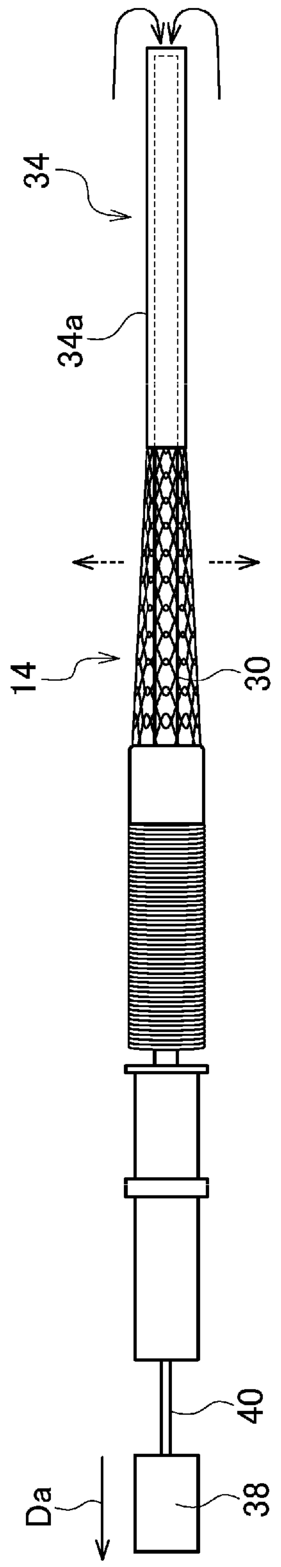
Figure 7C:
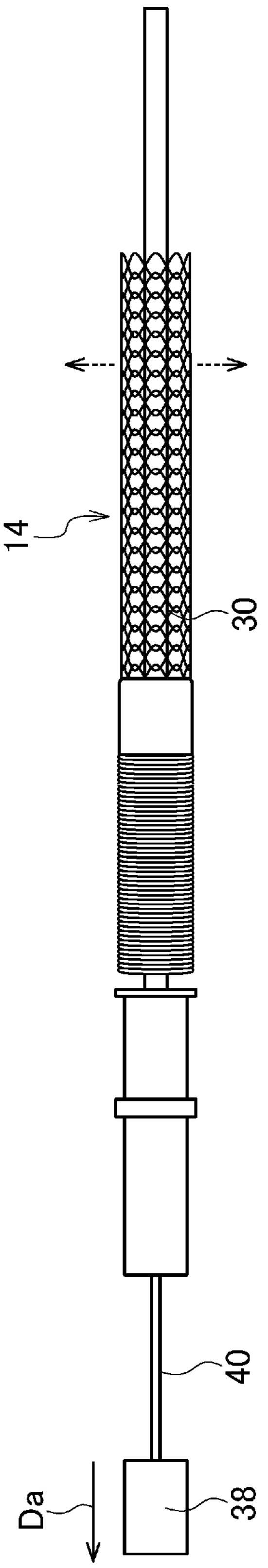

Description will be made with reference to FIGS. 7A to 7C. As illustrated in FIGS. 7A and 7B, a part of the cover 34 (here, inner part 34*b* of the cover 34 in FIG. 6) is pulled to the proximal end side by the first traction member 40 in conjunction with the first operating member 38 by the exposing operation Da with respect to the first operating member 38. This is followed by the movement of the outer peripheral part 34*a* of the cover 34 toward the distal end side in an axial direction, and the outer peripheral part 34*a* of the cover 34 is pulled into the shaft 30 from the distal end opening 30*b* of the shaft 30. As a result, the covered part of the stent body 14 by the outer peripheral part 34*a* of the cover 34 is gradually exposed by the axial pulling of the outer peripheral part 34*a* of the cover 34, and the stent body 14 at the covered part expands by a self-expanding force. As illustrated in FIG. 7C, the drawing mechanism 36 completes the exposing motion of the stent body 14, when the entire covered part of the stent body 14 covered by the cover 34 is exposed and the cover 34 no longer exists in a position that overlaps the outer side in the radial direction of the stent body 14.

Figure 8A:
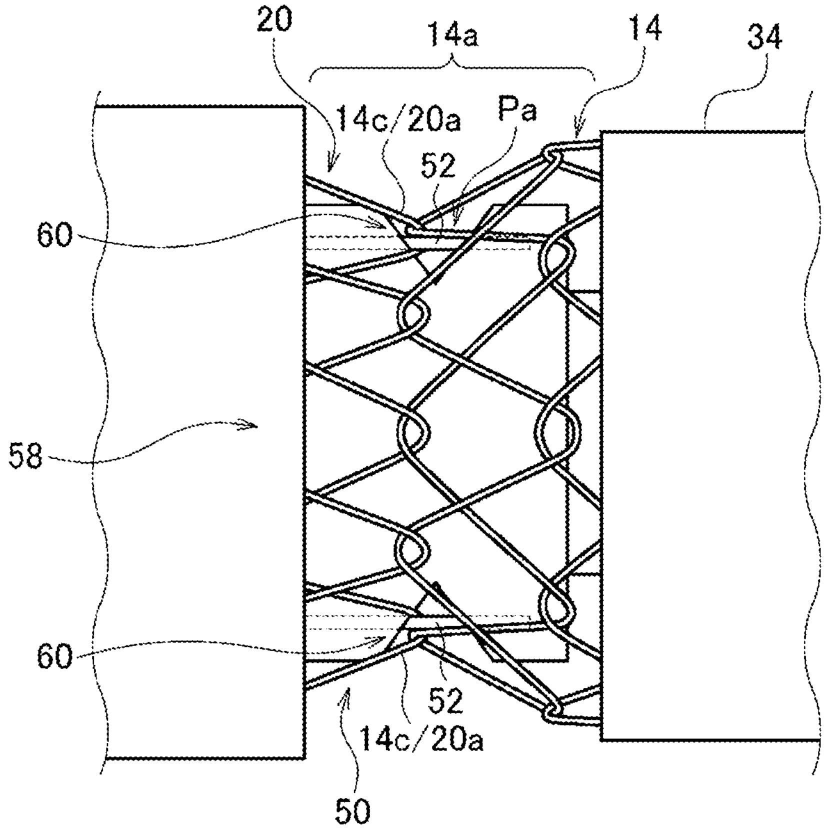
FIG. 8A is a schematic diagram illustrating a stent wire rod hooked on a restraining wire rod.

Description will be made with reference to FIGS. 5 and 8A. The delivery catheter 16 includes an expansion restraining mechanism 50, which is capable of restraining the expansion of the partial axial range of the stent body 14 and releasing the restraint. The expansion restraining mechanism 50 is provided with a plurality of restraining wire rods 52 to which the stent wire rods 14*c* constituting the stent body 14 are hooked, and a second operating member 54 that receives a releasing operation Db by the operator to release the restraint of the stent body 14 by the plurality of restraining wire rods 52. In addition, the expansion restraining mechanism 50 is provided with a wire rod fixing member 56, to which the plurality of restraining wire rods 52 are fixed and which pulls each restraining wire rod 52 to the proximal end side in conjunction with the releasing operation Db for the second operating member 54, and a displacement regulating member 58 that regulates the displacement of each of the plurality of restraining wire rods 52 on the outer side in the radial direction.

The second operating member 54 is operably attached to the handle 32. The second operating member 54 may be composed of a grip, a slide knob, a button, or the like. Here, an example in which the second operating member 54 can be moved and operated in the axial direction is described as an operation aspect, but the specific example is not particularly limited and may be a push operation, a rotation operation, or the like. The releasing operation Db for the second operating member 54 is performed by moving the second operating member 54 axially toward the proximal end side.

The wire rod fixing member 56 of the present embodiment is also used as the second operating member 54. The wire rod fixing member 56 may simply pull each restraining wire rod 52 toward the proximal end side in conjunction with the releasing operation Db for the second operating member 54, so that the specific configuration for this purpose is not particularly limited. For example, each restraining wire rod 52 may be pulled toward the proximal end side by connecting the second operating member 54 and the wire rod fixing member 56 with a second traction member such as a bar or wire, and pulling the wire rod fixing member 56 to the proximal end side with the second traction member in conjunction with the releasing operation Db for the second operating member 54.

The displacement regulating member 58 includes a distal end side displacement regulating part 58*a* provided farther at the distal end side than a hooking part 60 of the stent wire rods 14*c* to the restraining wire rods 52 and a proximal end side displacement regulating part 58*b* provided farther at the proximal end side than the hooking part 60. The distal end side displacement regulating part 58*a* is provided correspondingly to each of the plurality of restraining wire rods 52. The proximal end side displacement regulating part 58*b* is also provided correspondingly to each of the plurality of restraining wire rods 52. In the present embodiment, each of the distal end side displacement regulating part 58*a* and the proximal end side displacement regulating part 58*b* is configured by a hole extending axially through the displacement regulating member 58. The restraining wire rod 52 is inserted into the hole constituting each of the displacement regulating parts 58*a* and 58*b*. Each of the displacement regulating part 58*a* and 58*b* can regulate the displacement of the restraining wire rod 52 on the outer side in the radial direction by being in contact the restraining wire rod 52 from the outer side in the radial direction. In addition, each of the displacement regulating part 58*a* and 58*b* of the present embodiment can also regulate the displacement of the restraining wire rod 52 on the inner side in the radial direction by being in contact in the restraining wire rod 52 from the inner side in the radial direction. The displacement regulating member 58 includes a recess 58*c* positioned corresponding to the hooking part 60 of a stent wire rod 14*c* with respect to the restraining wire rod 52. The hooking part 60 of the stent wire rod 14*c* is located within the recess 58*c* of the displacement regulating member 58.

Figure 9:
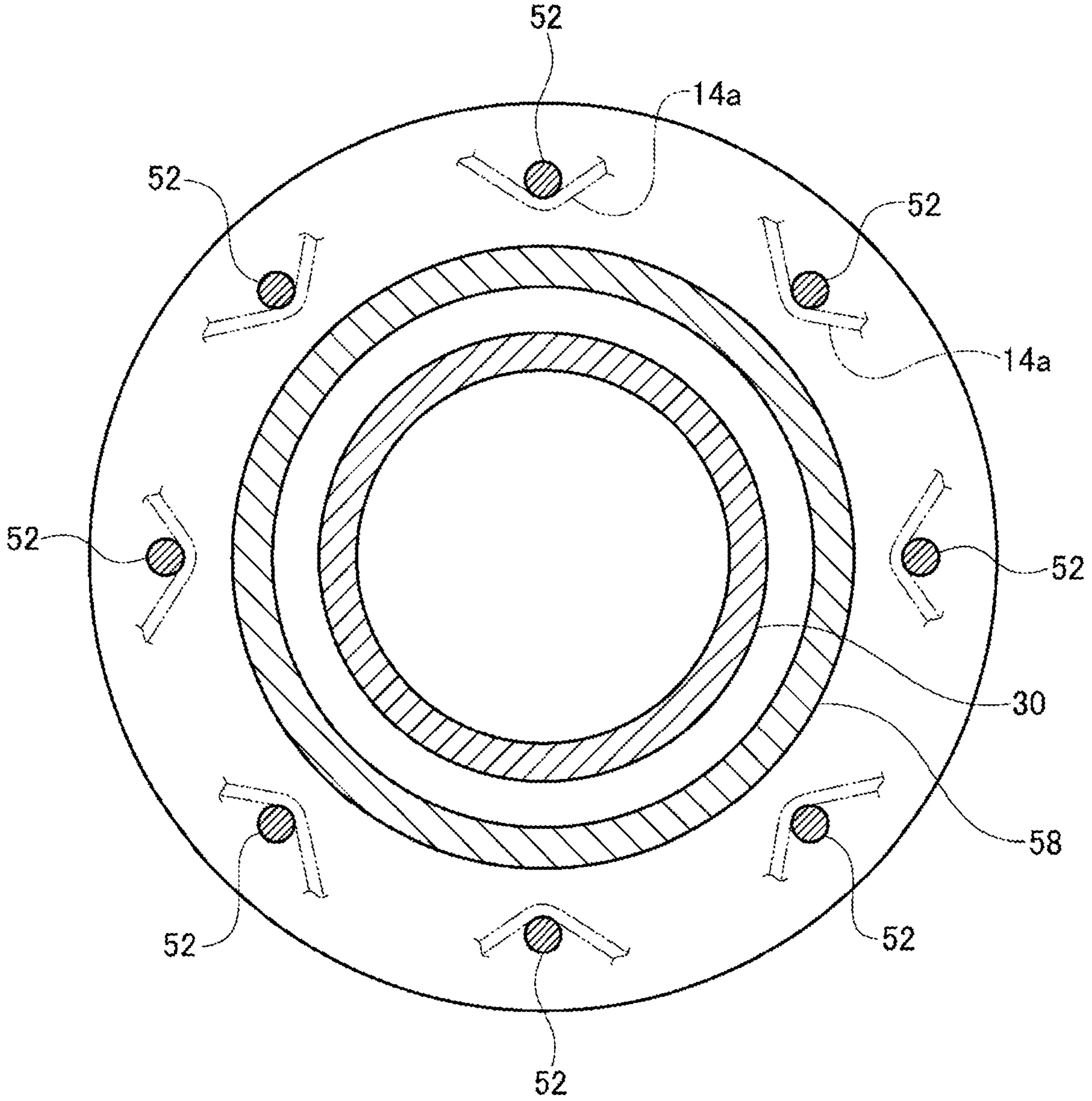
FIG. 9 is an A-A cross-sectional view of FIG. 5.

Description will be made with reference to FIGS. 5, 8A and 9. Each of the plurality of restraining wire rods 52 extends axially. The restraining wire rod 52 is, for example, a wire made of metal, resin, or the like. The stent wire rod 14*c* is hooked on the restraining wire rod 52 from the inner side of the restraining wire rod 52 in the radial direction. In the present embodiment, the stent wire rod 14*c* refers to the strand 20*a* of the stent 20 itself, but may also be a wire rod provided in the stent body 14 separately from the stent 20. FIG. 9 illustrates an example in which there are a total of eight restraining wire rods 52, but FIG. 8A or the like illustrates only two of these restraining wire rods 52. Each of the plurality of restraining wire rods 52 is hooked with the stent wire rod 14*c* from the inner side in the radial direction at a respective one of a plurality of circumferentially positions with spaces therebetween in the circumferential direction. By hooking the stent wire rods 14*c* from the inner side in the radial direction to the plurality of restraining wire rods 52, the expansion of the stent body 14 on the outer side in the radial direction in a partial axial range is restrained. The plurality of restraining wire rods 52 of the present embodiment restrain the expansion of an exposed part 14*a* of the stent body 14 exposed from the cover 34 at the proximal end portion 14*d* of the stent body 14.

FIG. 4 also illustrates the hooking part of the stent wire rod 14*c* with respect to the restraining wire rod 52. FIG. 4 is a view of the stent 20 when viewed from the outer side in the radial direction, and the back side of the paper in FIG. 4 is the inner side in the radial direction. In the present embodiment, the bent part 20*c* of the strand 20*a*, which constitutes the stent wire rod 14*c*, is hooked on the restraining wire rod 52. This makes it easier to hook the strand 20*a* rather than to hook intersections between the strands 20*a*.

The above delivery catheter 16 separably supports the indwelling device 12. To achieve this, the delivery catheter 16 supports, by the shaft 30, the stent body 14 that is maintained in a contracted state by the cover 34. Furthermore, the delivery catheter 16 can separate the indwelling device 12 by releasing the restraint of the stent body 14 by the expansion restraining mechanism 50 along with the exposing motion of the stent body 14 by the drawing mechanism 36. In addition, the delivery catheter 16 may detachably attach a part of the indwelling device 12 to a part of the delivery catheter 16 by using a string or the like. In this case, the indwelling device 12 can be separated by cutting the string, or the like, in addition to exposing motion of the stent body 14 by the drawing mechanism 36 and releasing the restraint by the expansion restraining mechanism 50.

The operation of the expansion restraining mechanism 50 described above will be described. Description will be made with reference to FIGS. 5 and 8A. In accordance with that the position for the above restraining wire rod 52 to receive the stent wire rod 14*c* shifts to the proximal end side in the axial direction, the stent wire rod 14*c* can be located from a hooking position Pa where the stent wire rod 14*c* is hooked, on a hooking release position Pb where the stent wire rod 14*c* is unhooked. When the plurality of restraining wire rods 52 are at the hooking position Pa, each stent wire rod 14*c* is hooked on respective one of the plurality of restraining wire rods 52, restraining the expansion of the stent body 14 in the partial axial range.

Figure 8B:
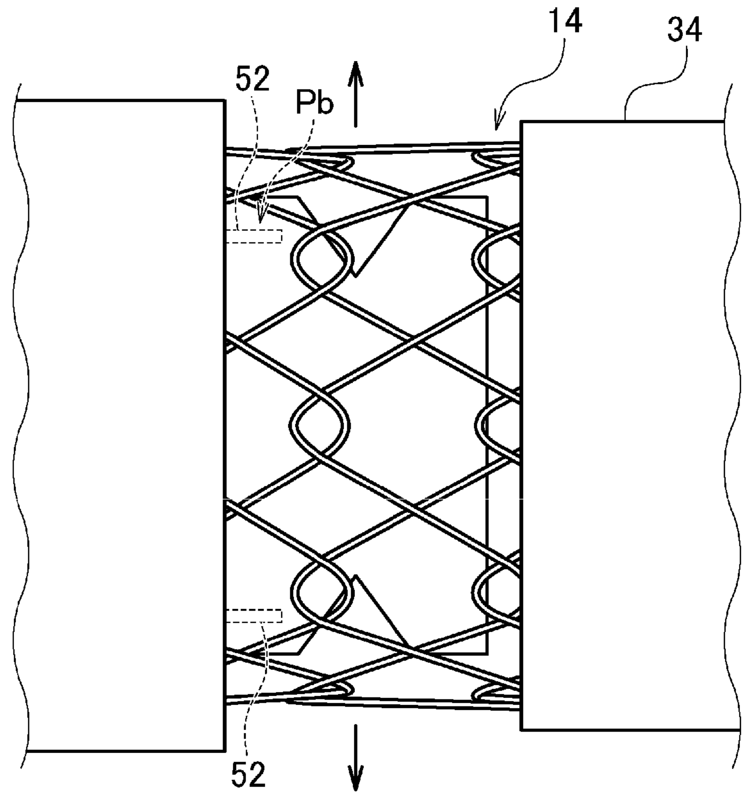
FIG. 8B is a schematic diagram illustrating the stent wire rod unhooked.

The releasing operation Db for the second operating member 54 causes the plurality of restraining wire rods 52 to be pulled to the proximal end side by the wire rod fixing member 56 in conjunction with the second operating member 54. This causes the plurality of restraining wire rods 52 to move from the hooking position Pa to the hooking release position Pb, as illustrated in FIG. 8B. As a result, the hooking of the stent wire rods 14*c* to the plurality of restraining wire rods 52 is collectively released, and the restraints of the stent body 14 by the plurality of restraining wire rods 52 are released. Along with this, the stent body 14 expands at the part restrained by the plurality of restraining wire rods 52, and the stent body 14 adheres to the luminal surface of the living organ at that part. Thus, the second operating member 54 of the present embodiment can release the hook of the stent body 14 with respect to each of the plurality of restraining wire rods 52 collectively by the releasing operation Db by the operator.

The expansion restraining mechanism 50 can release the restraint of the stent body 14 by the plurality of restraining wire rods 52, by moving, farther at the proximal end side than the hooking part 60 hooking the stent wire rods 14*c* with respect to the restraining wire rods 52, the constituent members of the expansion restraining mechanism 50 inside the indwelling device 12 to the proximal end side. Here, the constituent members of expansion restraining mechanism 50 refer to the plurality of restraining wire rods 52 in the present embodiment. This constituent member may be the wire rod fixing member 56 or the like in addition to the aforementioned traction member connecting the second operating member 54 and the wire rod fixing member 56. The constituent members of the expansion restraining mechanism 50 move inside the part surrounded by the stent body 14 farther at the proximal end side than the hooking part 60 as "inside the indwelling device 12" here. When the indwelling device 12 is provided with the tubular body 24 as in the present embodiment, the constituent members of the expansion restraining mechanism 50 also move inside the tubular body 24. In releasing the restraint of the stent body 14, these constituent members will not move to the proximal end side while being in contact the indwelling device 12 from the outer peripheral side farther at the proximal end side than the hooking part 60.

An example of operation of the above delivery device 10 will be described below. Here, as described above, the operation of the delivery device 10 using the OSG method will be described. In this OSG method, the chest of a living body is opened and then a part of the thoracic aorta 18 is incised. The indwelling device 12 is then delivered from the incision in the thoracic aorta 18 to the target site in the thoracic aorta 18 by using the delivery device 10. At this time, the indwelling device 12 is delivered with the handle 32 of the delivery catheter 16 gripped. Then, restraint of the stent body 14 is released by the expansion restraining mechanism 50, through the releasing operation Db for the second operating member 54 of the expansion restraining mechanism 50. Thus, the self-expanding force of the stent body 14 expands the part where expansion of the stent body 14 is restrained by the expansion restraining mechanism 50, so that the part adheres to the target site of the thoracic aorta 18. Before and after this, by the exposing operation Da for the first operating member 38 of the drawing mechanism 36, the exposing motion to expose the stent body 14 is performed. This exposes the covered part of the stent body 14, which is covered by the cover 34, and the exposed part is expanded by self-expanding force to adhere to the target site of the thoracic aorta 18. When expansion of the stent body 14 is completed, the delivery catheter 16 of the delivery device 10 is removed from the body by being pulled from the indwelling device 12 to the proximal end side. This is followed by any other necessary after-treatment to complete the treatment. The after-treatment here includes, for example, the work of anastomosing the cuff 26 of the indwelling device 12 with the blood vessel, and the work of anastomosing the proximal end side portion of the graft 28 of the indwelling device 12 with the blood vessel.

The effect of the delivery device 10 described above will be described. The delivery device 10 includes the plurality of restraining wire rods 52, which restrain the expansion of the stent body 14 and are separated from the cover 34. Thus, the expanding force acting on the cover 34 can be dispersed by each restraining wire rod 52. Thus, displacement of the cover 34 due to the expanding force of the stent body 14 can be suppressed, and a situation in which a part of the stent body 14 is unintentionally exposed and then expanded due to the displacement can be suppressed. As a result, this prevents the unintended expansion in the stent body 14 from interfering with the delivery, when the indwelling device 12 is delivered into the body.

Consider a case in which a partial expansion of the stent body 14 is left unrestrained and the indwelling device 12 is pushed into the body. In this case, the expanded part of the stent body 14 is in contact with the luminal surface of the living organ, increasing the push-in resistance. In this regard, according to the present embodiment, since the unintended expansion of the stent body 14 can be restrained, the push-in resistance when pushing the indwelling device 12 into the body can be reduced. In addition, the deformation of the stent 20 caused by pushing a part of the stent body 14 in an expanded state can be prevented.

The plurality of restraining wire rods 52 can release the restraint of the stent body 14 by moving in the axial direction. Thus, by axially moving the plurality of restraining wire rods 52, the hooking of the stent wire rods 14*c* to the restraining wire rods 52 can be reliably released and the hooking part 60 can be stably expanded. Additionally, when releasing the restraint of the stent body 14 by the plurality of restraining wire rods 52, it is not necessary to place separate members around the plurality of restraining wire rods 52, so that the increase of the outer diameter around the restraining wire rods 52 can be suppressed.

In particular, consider a case where the tubular body 24 with an outer diameter larger than the maximum outer diameter R34 of the cover 34 is connected farther at the proximal end side than the stent body 14. In this case, when the proximal end portion 14*d* of the stent body 14 unintentionally expands farther at the distal end side than the tubular body 24, the proximal end portion 14*d* tends to gradually increase the outer diameter toward the tubular body 24 side, and a problem occurs that the push-in resistance tends to increase. The plurality of restraining wire rods 52 of the present embodiment restrain the expansion of the proximal end portion 14*d* of such the stent body 14. Thus, it is advantageous in that the push-in resistance at such problematic parts can be reduced.

From this point of view, it is desirable that the part where the expansion of the stent body 14 is restrained by the plurality of restraining wire rods 52 is closer to the tubular body 24 at the proximal end portion 14*d* of the stent body 14, farther at the distal end side than the tubular body 24. In addition, when the stent body 14 is provided with the stent 20 using braided stent, the plurality of restraining wire rods 52 may restrain the expansion of the proximal end portion 14*d* of the stent body 14 in the part that constitutes the unit patterns 20*b* from the most proximal end side unit pattern 20*b* to the second one. In the present embodiment, the stent wire rods 14*c* are hooked on the plurality of restraining wire rods 52 at a plurality of circumferential positions in the part constituting the most proximal end side unit pattern 20*b*. In addition, the stent wire rods 14*c* may be hooked on the plurality of restraining wire rods 52 at a plurality of circumferential positions in the part constituting the second unit pattern 20*b* from the most proximal end side. In addition, when the stent body 14 is provided with a plurality of axially separated stents 20 (Z-stent, or the like), the plurality of restraining wire rods 52 may restrain the expansion of the proximal end portion 14*d* of the stent body 14 at the stent 20 on the most proximal end side.

Consider a case where a winding member such as a ring member wound around the outer peripheral side of the stent body 14 is used as a restraint member to restrain the expansion of the stent body 14. In this case, the outer diameter increases by the amount of the winding member at the part to intend restraint of the expansion of the stent body 14, so that the push-in resistance remains large. In this respect, according to the present embodiment, the plurality of restraining wire rods 52 are used as restraint members. Thus, it is not necessary to wind the restraint member at the location to intend restraint of the expansion of the stent body 14, so that the increase in the outer diameter caused by the winding can be avoided. As a result, compared with the case where the winding member is used as the restraint member, the outer diameter at the part to intend to restrain the expansion of the stent body 14 is easily reduced, so that the push-in resistance can be reduced.

When a winding member is used as a restraint member, it is necessary to release the restraint of the stent body 14 by the winding member, by causing the constituent members (such as a winding member) of the expansion restraining mechanism 50 to move while being in contact with the indwelling device 12 from the outer peripheral side. Thus, when releasing the restraint of the stent body 14 by the winding member, the constituent members of the expansion restraining mechanism 50 interfere greatly with the indwelling device 12.

In this regard, the expansion restraining mechanism 50 of the present embodiment can release the restraint of the stent body by moving the constituent members of the expansion restraining mechanism 50 (here, the restraining wire rods 52) inside the indwelling device 12 farther at the proximal end side than the hooking part 60. Thus, in releasing the restraint of the stent body 14, the constituent members of the expansion restraining mechanism 50 do not significantly interfere with the indwelling device 12, and the release operation can be facilitated. In particular, when the delivery device 10 is used, the state of the indwelling device 12 is often under invisible circumstance. It is advantageous in that large interference with the indwelling device 12 can be avoided under such invisible circumstance.

The plurality of restraining wire rods 52 restrain the expansion of the exposed part 14*a* of the stent body 14 exposed from the cover 34. Thus, the cover 34 need not cover the hooking part 60 of the stent wire rod 14*c* with respect to the restraining wire rod 52, thereby suppressing the increase in the outer diameter around that hooking part 60.

When the stent wire rod 14*c* is hooked on the plurality of restraining wire rods 52 at a plurality of circumferential positions, an expanding force toward the outer side acts in the radial direction on the part receiving the stent wire rod 14*c* at the restraining wire rod 52, and each of the plurality of restraining wire rods 52 tends to displace on the outer side in the radial direction. According to the present embodiment, the displacement regulating member 58 is provided to regulate the displacement of each of the plurality of restraining wire rods 52 on the outer side in the radial direction. Thus, the displacement of each of the plurality of restraining wire rods 52 caused by the expanding force of the plurality of restraining wire rods 52 can be regulated on the outer side in the radial direction, and the stent body 14 can be stably maintained in a small, contracted state at the hooking part 60 of the stent wire rod 14*c*.

The expansion restraining mechanism 50 can unhook the stent wire rods 14*c* with respect to the respective ones of the plurality of restraining wire rods 52 collectively. Thus, compared with the case of individually releasing the hooking of the stent wire rod 14*c* for each of the plurality of restraining wire rods 52, the operation for releasing the hooking of the stent wire rod 14*c* can be simplified.

Second Embodiment

Figure 10A:
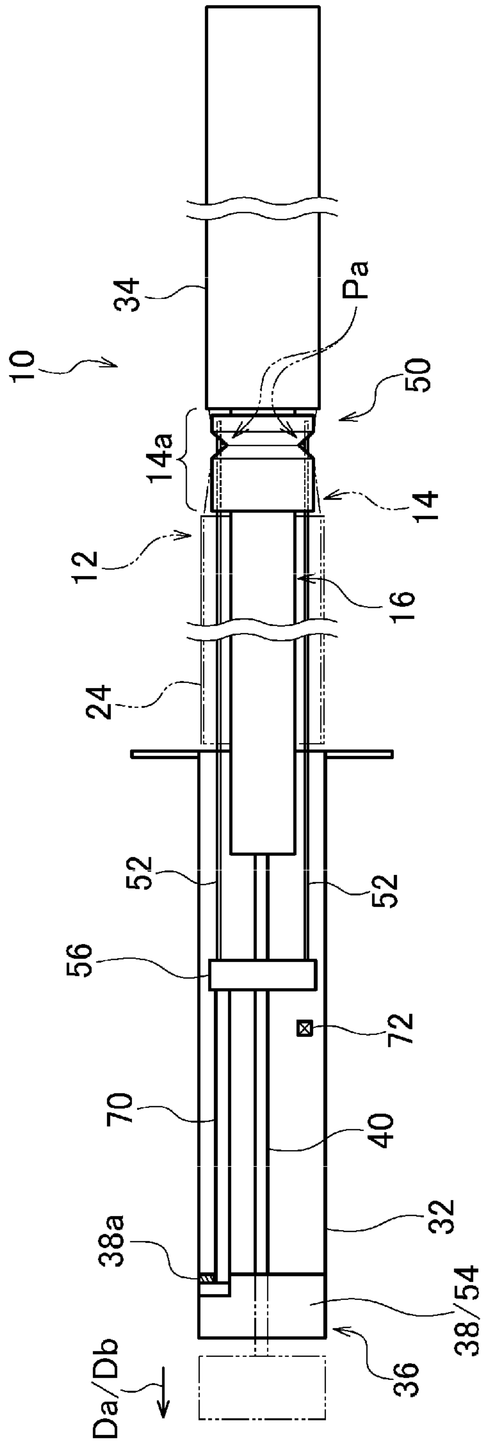
FIGS. 10A to 10B are schematic diagrams illustrating operations of the delivery device of a second embodiment.
Figure 10B:
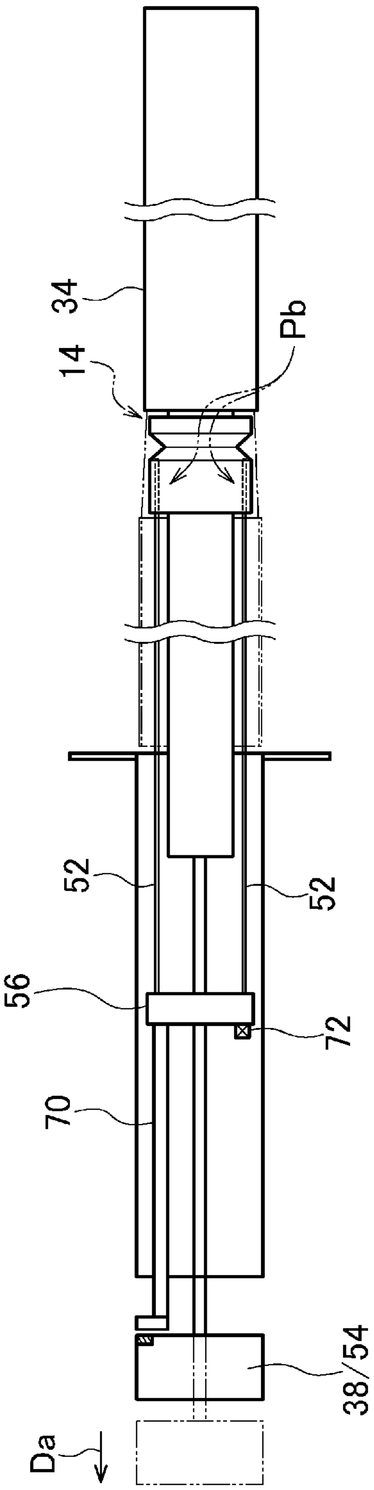

Description will be made with reference to FIGS. 10A and 10B. In the subsequent embodiment, the same content as in the first embodiment may be applied to the components which are described in the first embodiment but not described below. Additionally, the delivery device 10 in the subsequent embodiment can exhibit the same effect as that described in the first embodiment.

The case where the expansion restraining mechanism 50 of the first embodiment does not work with the drawing mechanism 36 has been described. The expansion restraining mechanism 50 of the present embodiment can release the restraint of the stent body 14 in conjunction with the drawing mechanism 36.

The expansion restraining mechanism 50 includes an attachment member 70 fixed to the wire rod fixing member 56 and separably attached to a receptacle 38*a* of the first operating member 38, and a regulating member 72 fixed to the handle 32 and capable of regulating axial movement of the wire rod fixing member 56 toward the proximal end side. In the present embodiment, the first operating member 38 is also used as the second operating member 54 of the expansion restraining mechanism 50. The releasing operation Db for the second operating member 54 is also used as the exposing operation Da for the first operating member 38. In the present embodiment, the wire rod fixing member 56 of the expansion restraining mechanism 50 is provided separately from the second operating member 54 (first operating member 38).

The attachment member 70 of the present embodiment is an elastic claw with its own elastic deformation hooked on the receptacle 38*a* of the first operating member 38, and can be separated from the first operating member 38 by releasing the hook on the receptacle 38*a*. In this case, the receptacle 38*a* is composed of a claw receptacle provided at the first operating member 38. Specific examples of the attachment member 70 and the receptacle 38*a* are not limited and may be a combination of magnets, or the like. The attachment member 70 is separable from the first operating member 38 when the exposing operation Da for the first operating member 38 continues with the axial movement, toward the proximal end side, of the wire rod fixing member 56 regulated by the regulating member 72. The regulating member 72 can regulate the axial movement of the wire rod fixing member 56 toward the proximal end side by being in contact with the wire rod fixing member 56 or a member (e.g., attachment member 70) that can be moved integrally with the wire rod fixing member 56.

The operation of the expansion restraining mechanism 50 and the drawing mechanism 36 above is described below. When the exposing operation Da (the releasing operation Db by the second operating member 54) by the first operating member 38 is started, the wire rod fixing member 56 moves axially toward the proximal end side with the attachment member 70 attached to the first operating member 38. Consequently, as illustrated in FIG. 10B, the movement of the plurality of restraining wire rods 52 from the hooking position Pa to the hooking release position Pb releases the hooking of the stent wire rods 14*c* (not illustrated) with respect to the plurality of restraining wire rods 52 and releases the restraint of the stent body 14 by the expansion restraining mechanism 50. The regulating member 72 is provided in a position that does not regulate the movement of the wire rod fixing member 56 until the plurality of restraining wire rods 52 move to the hooking release position Pb. When the exposing operation Da for the first operating member 38 then continues, the axial movement, toward the proximal end side, of the wire rod fixing member 56 is regulated by the regulating member 72. In this state, continuing the exposing operation Da for the first operating member 38 causes the attachment member 70 to separate from the first operating member 38. From this point on, when the exposing operation Da by the first operating member 38 continues, only the first operating member 38 moves axially toward the proximal end side while the first operating member 38 remains separated from the wire rod fixing member 56, and the exposing motion to expose the covered part of the stent body 14 is started.

The above wire rod fixing member 56 is separably attached to the first operating member 38 (second operating member 54) via the attachment member 70 in conjunction with the releasing operation Db for the second operating member 54. In addition, since the wire rod fixing member 56 separates from the first operating member 38 after the restraint of the stent body 14 by the expansion restraining mechanism 50 is released, it becomes impossible for the wire rod fixing member 56 to move axially to the proximal end side even when exposing operation Da by the first operating member 38 continues thereafter.

Thus, the expansion restraining mechanism 50 can release, in conjunction with the drawing mechanism 36, restraint of the stent body 14. By one operation (exposing operation Da used also as the releasing operation Db) of the operator on the first operating member 38, which is served by the second operating member 54, the covered part of the stent body 14 is exposed by the drawing mechanism 36, as well as the restraint of the stent body 14 by the expansion restraining mechanism 50 can be released. This reduces the number of operations performed by the operator, as compared to the case where operations for the drawing mechanism 36 and operations for the expansion restraining mechanism 50 are performed separately.

In particular, the expansion restraining mechanism 50 of the present embodiment can release the restraint of the stent body 14 before starting the exposing motion to expose the covered part of the stent body 14, which is covered by the cover 34. Here, "before starting the exposing motion" means a time from the start of the exposing operation Da by the first operating member 38 to the start of the exposure of the covered part of the stent body 14 by the cover 34. This will allow early release of restraints by the expansion restraining mechanism 50 in conjunction with the drawing mechanism 36. As a result, the axial position of the indwelling device 12 with respect to the living organ can be positioned at an early stage by sticking, to the luminal surface of the living organ, the part restrained by the expansion restraining mechanism 50 in the stent body 14.

In relation to such effects, the expansion restraining mechanism 50 may be able to release the restraint of the stent body 14 immediately after starting the exposing motion of the stent body 14. Here, "immediately after the starting the exposing motion" is defined as the period from the start of the exposure of the covered part of the stent body 14 by the cover 34 to the start of the exposure of the stent body 14 by an axial length equal to 1/10 of the total axial length of a covered part 14*b* (see FIG. 6) of the stent body 14 by the cover 34.

Third Embodiment

Description will be made with reference to FIGS. 11A to 11D. FIGS. 11A to 11D are explanatory diagrams for illustrating the operation of the delivery device 10 of a third embodiment. Unlike the second embodiment, the expansion restraining mechanism 50 of the present embodiment can release the restraint of the stent body 14 in conjunction with the completion of the exposing motion of the stent body 14 by the drawing mechanism 36. The expansion restraining mechanism 50 includes a stopper 80 fixed to the first traction member 40, a stopper receiver 82 capable of receiving the stopper 80 when the stopper 80 moves axially toward the proximal end side together with the first traction member 40, and a fixing member 84 fixed to the wire rod fixing member 56 as well as to the stopper receiver 82. The first traction member 40 is slidably inserted into the stopper receiver 82 of the present embodiment. By the first traction member 40 moving axially toward the proximal end side in a state of receiving the stopper 80, the stopper receiver 82 can move axially toward the proximal end side together with the stopper 80. The first operating member 38 is also used as the second operating member 54 of the expansion restraining mechanism 50 in the present embodiment, as in the second embodiment. Furthermore, in the present embodiment, the wire rod fixing member 56 of the expansion restraining mechanism 50 is also provided separately from the second operating member 54 (first operating member 38), as in the second embodiment.

Figure 11A:
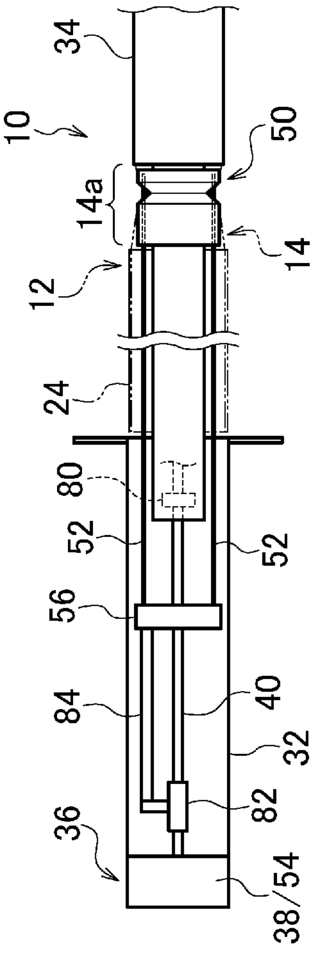
FIGS. 11A to 11D are schematic diagrams illustrating operations of the delivery device of a third embodiment.
Figure 11B:
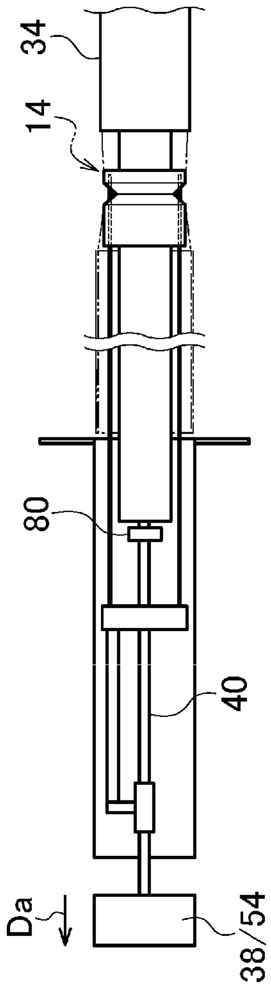

The operation of the expansion restraining mechanism 50 and the drawing mechanism 36 above is described below. The exposing operation Da (releasing operation Db by the second operating member 54) is started by the first operating member 38 as illustrated in FIG. 11B. As a result, a part of the cover 34 is pulled toward the proximal end side by the first traction member 40, so that the covered part of the stent body 14 by the cover 34 starts to be exposed due to the cover

Figure 11C:
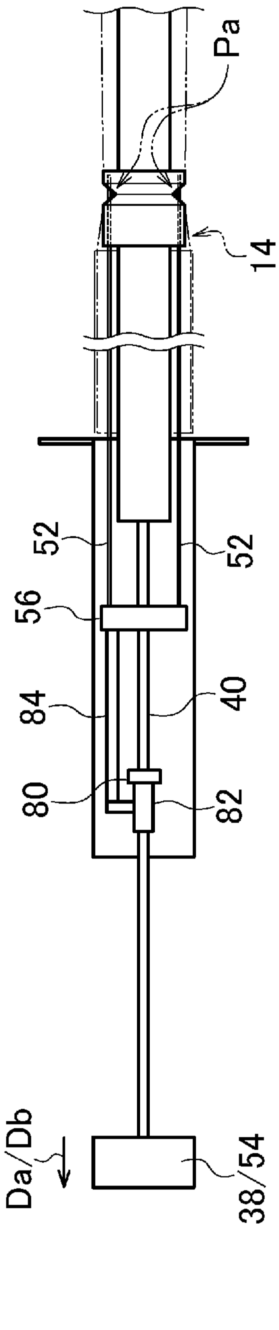
Figure 11D:
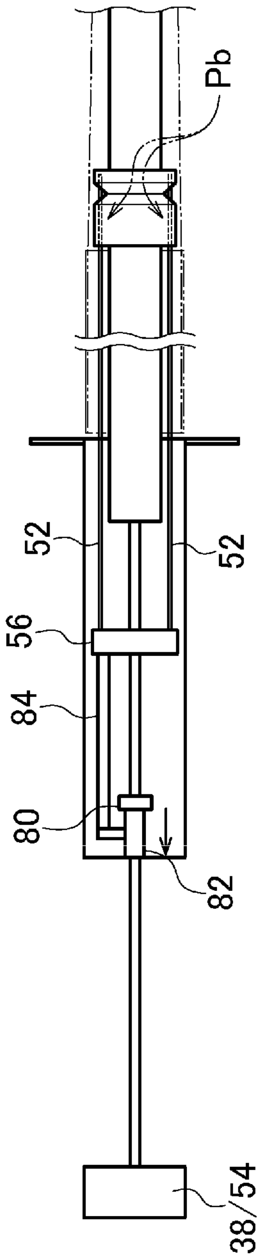

34 being pulled axially. Then, as illustrated in FIG. 11C, when the exposing operation Da by the first operating member 38 continues after the entire covered part of the stent body 14 covered by the cover 34 is exposed, the stopper 80 fixed to the first traction member 40 is in contact with the stopper receiver 82. When the exposing operation Da (releasing operation Db by the second operating member 54) by the first operating member 38 continues in this state, the wire rod fixing member 56 moves axially toward the proximal end side together with the fixing member 84 by the stopper receiver 82. Thus, as illustrated in FIG. 11D, the movement of the plurality of restraining wire rods 52 from the hooking position Pa to the hooking release position Pb releases the hooking of the stent wire rods 14*c* (not illustrated) with respect to the plurality of restraining wire rods 52 and releases the restraint of the stent body 14 by the expansion restraining mechanism 50.

The wire rod fixing member 56 described above will not move axially toward the proximal end side without conjunction with the exposing operation Da for the first operating member 38 until the exposing motion of the stent body 14 is completed. In addition, the wire rod fixing member 56 will be able to move axially toward the proximal end side in conjunction with the exposing operation Da for the first operating member 38 after the stent body 14 completes the exposing motion. Here, "completing the exposing motion" means, as described above, that the entire covered part of the stent body 14 covered by the cover 34 is exposed and that the cover 34 does not exist at a position that overlaps on the outer side in the radial direction of the stent body 14. Since the expansion restraining mechanism 50 described above can also release the restraint of the stent body 14 in conjunction with the drawing mechanism 36 as in the second embodiment, the number of operations by the operator can be reduced.

In addition, the expansion restraining mechanism 50 of the present embodiment can release the restraint of the stent body 14 in conjunction with the drawing mechanism 36 after the completion of the exposing motion of the stent body 14 by the drawing mechanism 36. To achieve this, after completing the exposing motion of the stent body 14 by performing the exposing operation Da with the first operating member 38, the expansion restraining mechanism 50 can release the restraint of the stent body 14 by continuing the exposing operation Da (releasing operation Db) of the stent body 14.

Thus, by hooking the stent wire rods 14*c* on the restraining wire rods 52 until the exposing motion of the stent body 14 completes, displacement of the indwelling device 12 with respect to the delivery catheter 16 in the axial direction can be suppressed. Such displacement of the indwelling device 12 is caused by the application of friction force from the cover 34 to the stent body 14 during the exposing motion of the stent body 14. By suppressing such displacement of the indwelling device 12 during the exposing motion of the stent body 14, accuracy can be improved in placing the indwelling device 12 at the target position. Additionally, there exists an advantage of eliminating the need for other members (threads, or the like) connecting the stent body 14 and the delivery catheter 16 in order to prevent the displacement of the indwelling device 12.

In relation to such effects, the expansion restraining mechanism 50 may be able to release the restraint of the stent body 14 immediately before completing the exposing motion of the stent body 14. Here, "immediately before completing the exposing motion of the stent body 14" is defined as a period from when the stent body 14 begins to be exposed by an axial length of 9/10 with respect to the total axial length of the covered part 14*b* (see FIG. 6) covered by the cover 34, of the stent body 14 until completion of the exposing motion of the stent body 14.

Modifications of the above components are described below.

The indwelling device 12 may not include the tubular body 24. The outer diameter R24 at the distal end portion of the tubular body 24 may be less than or equal to the maximum outer diameter R34 of the cover 34. Specific examples of the tubular body 24 are not particularly limited. The tubular body 24 may include only one of, for example, the graft 28 and the cuff 26, or may have other configurations.

The drawing mechanism 36 is described above with the example of pulling the cover 34 in the axial direction along with the axial movement of the outer peripheral part 34*a* of the cover 34 toward the distal end side. Alternatively, the drawing mechanism 36 may pull the cover 34 axially along with an axial movement toward the proximal end side, of the outer peripheral part 34*a* of the cover 34. In this case, the cover 34 may include only the outer peripheral part 34*a* without a duplex structure.

The specific structure for achieving the expansion restraining mechanism 50 is not particularly limited. For example, in conjunction with the second operating member 54 and the wire rod fixing member 56, both may be connected via other members such as the second traction member mentioned above. Constituent members of the expansion restraining mechanism 50 may be able to release the restraint of the stent body 14 by moving outside the indwelling device 12 farther at the proximal end side than the hooking part 60 of the stent wire rod 14*c* with respect to the restraining wire rod 52.

In the example described, the plurality of restraining wire rods 52 restrain the expansion of the proximal end portion 14*d* of the stent body 14. However, the part to restrain the expansion may not be particularly limited, and the expansion of either the distal end portion or the middle portion of the stent body 14 may be restrained. The plurality of restraining wire rods 52 may also restrain the expansion of the covered part 14*b* of the stent body 14 covered by the cover 34, in addition to the exposed part 14*a* of the stent body 14 exposed from the cover 34. In releasing the restraint of the stent body 14, the plurality of restraining wire rods 52 are not particularly limited in the direction of moving in the axial direction at the part receiving the stent wire rod 14*c*, and the direction may be either toward the proximal end side or the distal end side.

When the expansion restraining mechanism 50 is in conjunction with the drawing mechanism 36, a before-and-after relation between the timing of the exposing motion by the drawing mechanism 36 and the timing of releasing restraint of the stent body 14 by the expansion restraining mechanism 50 is not particularly limited. For example, the restraint of the stent body 14 by the expansion restraining mechanism 50 may be released at any time during the exposing motion by the drawing mechanism 36.

Specific examples for releasing the restraint of the stent body 14 by the expansion restraining mechanism 50 in conjunction with the drawing mechanism 36 are not particularly limited. For example, the attachment member 70 may be inseparably attached to the first operating member 38 when the attachment member 70 fixed to the wire rod fixing member 56 is attached to the first operating member 38 as in the second embodiment. The wire rod fixing member 56 may be used as the stopper receiver 82 in moving the stopper receiver 82 axially toward the proximal end side by the stopper 80 fixed to the first traction member 40 as in the third embodiment. In addition, when releasing the restraint of the stent body 14 before or immediately after starting the exposing motion by the drawing mechanism 36 as in the second embodiment, the stopper 80 fixed to the first traction member 40 and the stopper receiver 82 receiving the stopper 80 may be used as in the third embodiment. Further, specific examples for separably attaching the attachment member 70 of the expansion restraining mechanism 50 to the first operating member 38 are not particularly limited. To achieve this, the example of using the regulating member 72 in the second embodiment is described above, but this is not required.

The expansion restraining mechanism 50 need not include the displacement regulating member 58. The displacement regulating member 58 is only required to be able to regulate the displacement of the plurality of restraining wire rods 52 on the outer side in the radial direction. Thus, it is not essential to regulate the displacement on the inner side in the radial direction, and the specific structure for this purpose is not particularly limited. For example, the displacement regulating member 58 may include only one of the distal end side displacement regulating part 58*a* and the proximal end side displacement regulating part 58*b*. In addition, each displacement regulating part 58*a*, 58*b* of the displacement regulating member 58 may be, instead of a hole, composed of a ring shape, a tubular shape or the like that can hook the restraining wire rod 52. The expansion restraining mechanism 50 may include a separate second operating member 54 for individually unhooking the stent body 14 for each individual restraining wire rod 52.

The above embodiments and modifications are illustrative. Technical ideas obtained by being abstracted should not be interpreted as limited to the contents of the embodiments and modifications. Numerous design changes, such as variations, addition, and deletion of components, can be made to the contents of the embodiments and modifications. In the embodiments described above, the content in which such design changes can be made has been emphasized with expressions such as of "the embodiment". However, design changes are also possible even in the content without such an expression. Hatching in sections of the drawings does not limit the material of a hatched object. Structures and numerical values referred to in the embodiments and the modifications naturally include those that can be regarded as the same in consideration of manufacturing errors and the like.

While preferred embodiments of the disclosure have been described above, it is to be understood that variations and modifications will be apparent to those skilled in the art without departing from the scope and spirit of the disclosure. The scope of the disclosure, therefore, is to be determined solely by the following claims.

The invention claimed is:

1. A delivery device comprising:

an indwelling device including a stent body that is self-expandable; and a delivery catheter configured to separably support the indwelling device, wherein the delivery catheter includes:

a cover configured to cover at least a part of an axial range of the stent body; and an expansion restraining mechanism including a plurality of restraining wire rods configured to restrain expansion of the stent body by hooking a stent wire rod that constitutes the stent body, the plurality of restraining wire rods are configured to release restraint of the stent body by moving axially, and the expansion restraining mechanism is configured to release the restraint of the stent body by a constituent member of the expansion restraining mechanism moving inside the indwelling device farther at a proximal end side than a hooking part of the stent wire rod with respect to the plurality of restraining wire rods.

2. The delivery device according to claim 1, wherein the plurality of restraining wire rods restrain expansion of an exposed part of the stent body exposed from the cover.

3. The delivery device according to claim 1, wherein the expansion restraining mechanism includes a displacement regulating member which regulates displacement of each of the plurality of restraining wire rods on an outer side in a radial direction.

4. The delivery device according to claim 1, wherein the delivery catheter further includes a drawing mechanism which axially pulls the cover, and the expansion restraining mechanism is configured to release the restraint of the stent body in conjunction with the drawing mechanism.

5. The delivery device according to claim 4, wherein the drawing mechanism performs an exposing motion by axially pulling the cover to expose a covered part of the stent body, the covered part being covered with the cover, and the expansion restraining mechanism releases the restraint of the stent body before or immediately after start of the exposing motion by the drawing mechanism.

6. The delivery device according to claim 4, wherein the drawing mechanism performs an exposing motion by axially pulling the cover to expose a covered part of the stent body, the covered part being covered with the cover, and the expansion restraining mechanism releases the restraint of the stent body immediately before or after completion of the exposing motion by the drawing mechanism.

7. The delivery device according to claim 1, wherein the expansion restraining mechanism includes an operating member configured to collectively release hooking of the stent wire rod with respect to each of the plurality of restraining wire rods.

8. The delivery device according to claim 1, wherein the indwelling device includes a tubular body positioned at the proximal end side with respect to the stent body, the tubular body being connected to the stent body, an outer diameter of a distal end portion of the tubular body is larger than a maximum outer diameter of the cover, and the plurality of restraining wire rods restrain expansion of a proximal end portion of the stent body.

* * * * *